US006613808B2

(12) United States Patent
Schwarz et al.

(10) Patent No.: US 6,613,808 B2
(45) Date of Patent: Sep. 2, 2003

(54) FISCHER-TROPSCH PROCESSES AND CATALYSTS USING POLYACRYLATE MATRIX STRUCTURES

(75) Inventors: Stephan Schwarz, Wilmington, DE (US); Sergej A. Maslov, Ponca City, OK (US)

(73) Assignee: Conoco Inc., Houston, TX (US)

( * ) Notice: Subject to any disclaimer, the term of this patent is extended or adjusted under 35 U.S.C. 154(b) by 171 days.

(21) Appl. No.: 09/880,451

(22) Filed: Jun. 13, 2001

(65) Prior Publication Data

US 2002/0183404 A1 Dec. 5, 2002

Related U.S. Application Data

(60) Provisional application No. 60/211,084, filed on Jun. 12, 2000.

(51) Int. Cl.[7] ............................ C07C 27/00; C07C 27/06
(52) U.S. Cl. ...................... 518/715; 518/713; 518/714; 518/700; 518/719; 518/720; 518/721
(58) Field of Search ...................... 518/700, 715, 518/720, 719, 721, 713, 714

(56) References Cited

U.S. PATENT DOCUMENTS

| | | | | | |
|---|---|---|---|---|---|
| 4,179,402 | A | * | 12/1979 | Kim et al. ................ | 502/159 |
| 4,181,675 | A | * | 1/1980 | Makin et al. ............. | 518/705 |
| 4,230,633 | A | | 10/1980 | Vollhardt et al. ..... | 260/449.6 M |
| 4,292,415 | A | | 9/1981 | Vollhardt et al. .......... | 525/357 |
| 4,725,568 | A | | 2/1988 | Parker et al. ............. | 502/159 |

FOREIGN PATENT DOCUMENTS

| EP | 0005569 | 11/1979 |
|---|---|---|

OTHER PUBLICATIONS

Gerald, C. Grunewald and Russell S. Drago, "Reduction of Carbon Monoxide and Dioxide by Metal Carbonyls on a Pyrolysed Polymeric Support", J. Chem. Soc., Chem. Commun., 3–5, (1988).

Kenzi Tamaru, "Heterogeneous Catalysis by Electron Donor–Acceptor Complexes of Alkali Metals", Catalysis Reviews, 4(2), 161–178 (1970).

Gerald C. Grunewald and Russell S. Drago, "Reduction of Carbon Monoxide and Dioxide by Metal Carbonyls on a Pyrolysed Polymeric Support", J. Chem. Soc., Chem, Commun., 3–5, (1988).

Jean–Claude Carlu, et al, "Fischer–Tropsch Synthesis Catalyzed by Iron Catalyst Supported on Porous Polymers., I. Synthesis of the Supported Catalyst and Study of the Repartition of the Catalyst in the Polymeric Support", Reactive Polymers, 9, Elsevier Science Publishers, B.V., Amsterdam, 119–128, (1988).

Jean–Claude Carlu, Claude Caze, "Fischer–Tropsch Synthesis Catalyzed By Iron Catalyst Supported on Porous Polymers., I. Synthesis of the Supported Catalyst and Study of the Repartition of the Catalyst in The Polymeric Support", Reactive Polymers, 9, Elsevier Science Publishers, B.V., Amsterdam, 119–128, (1988).

Abraham Warshawsky, and Donald A. Upson, "*Zerovalent metal–polymer composites via electroless deposition on functional polymers*", Polymer, vol. 30, 972–973, (1989).

E. Iglesia et al, "Computer–Aided Design of Catalysts", E. Robert Becker et al, New York, Marcel Dekker, Inc., 215, (1993).

Ion Udrea, Olga Butufei, Magdalena Mazare, Dorin Crisan, "*Poliaminoclorchinone. IV. Hidrogenareaa monoxidului de carbon pe catalizatori de fier depus pe suporti polymerici si anorganici*", Materiale Plastice 33, No. 3, 155–159, (1996).

PCT Search Report for PCT/US01/18997 Dated Nov. 13, 2001.

* cited by examiner

*Primary Examiner*—Jafar Parsa
(74) *Attorney, Agent, or Firm*—Conley Rose & Tayon

(57) ABSTRACT

A Fischer-Tropsch catalyst comprising a catalytically active first metal selected from the group consisting of at least one metal selected from the group consisting of iron, nickel, cobalt, chromium, and mixtures thereof, at least one second metal selected from the group consisting of silver, iron, zinc, copper, platinum, zirconium and combinations thereof; and a matrix structure comprising a polymer selected from the group consisting of polyacrylates and polymethacrylates. The first and second metals are incorporated into the polymer.

14 Claims, No Drawings

FISCHER-TROPSCH PROCESSES AND CATALYSTS USING POLYACRYLATE MATRIX STRUCTURES

RELATED APPLICATIONS

This application claims benefit of priority from U.S. Ser. No. 60/211,084, filed Jun. 12, 2000 and entitled "Fischer-Tropsch Processes and Catalysts Using Polyacrylate Support," which is incorporated herein by reference.

STATEMENT REGARDING FEDERALLY SPONSORED RESEARCH OR DEVELOPMENT

Not applicable.

TECHNICAL FIELD OF THE INVENTION

The present invention relates to a process for the preparation of hydrocarbons from synthesis gas, i.e., a mixture of carbon monoxide and hydrogen, typically labeled the Fischer-Tropsch process. More particularly, this invention relates to the use of acrylate polymer matrix structures for catalysts for the Fischer-Tropsch process. Still more particularly, the present invention relates to Fischer-Tropsch catalysts formed by polymerizing an acrylate with a catalytically active metal.

BACKGROUND

Large quantities of methane, the main component of natural gas, are available in many areas of the world, and natural gas is predicted to outlast oil reserves by a significant margin. However, most natural gas is situated in areas that are geographically remote from population and industrial centers. The costs of compression, transportation, and storage make its use economically unattractive. To improve the economics of natural gas use, much research has focused on the use of methane as a starting material for the production of higher hydrocarbons and hydrocarbon liquids, which are more easily transported and thus more economical. The conversion of methane to hydrocarbons is typically carried out in two steps. In the first step, methane is converted into a mixture of carbon monoxide and hydrogen (i.e., synthesis gas or syngas). In a second step, the syngas is converted into hydrocarbons.

This second step, the preparation of hydrocarbons from synthesis gas, is well known in the art and is usually referred to as Fischer-Tropsch synthesis, the Fischer-Tropsch process, or Fischer-Tropsch reaction(s). Fischer-Tropsch synthesis generally entails contacting a stream of synthesis gas with a catalyst under temperature and pressure conditions that allow the synthesis gas to react and form hydrocarbons.

More specifically, the Fischer-Tropsch reaction is the catalytic hydrogenation of carbon monoxide to produce any of a variety of products ranging from methane to higher alkanes and aliphatic alcohols. Research continues on the development of more efficient Fischer-Tropsch catalyst systems and reaction systems that increase the selectivity for high-value hydrocarbons in the Fischer-Tropsch product stream.

There are continuing efforts to find catalysts that are more effective at producing these desired products. Product distribution, product selectivity, and reactor productivity depend heavily on the type and structure of the catalyst and on the reactor type and operating conditions. It is particularly desirable to maximize the production of high-value liquid hydrocarbons, such as hydrocarbons with five or more carbon atoms per hydrocarbon chain ($C_{5+}$).

Catalyst supports for catalysts used in Fischer-Tropsch synthesis of hydrocarbons have typically been oxides (e.g., silica, alumina, titania, zirconia or mixtures thereof, such as silica-alumina). The products prepared by using these catalysts usually have a very wide range of molecular weights. It has been asserted that the Fischer-Tropsch synthesis reaction is only weakly dependent on the chemical identity of the metal oxide support (see E. Iglesia et al. 1993, In: "Computer-Aided Design of Catalysts," ed. E. R. Becker et al., p. 215, New York, Marcel Dekker, Inc.). Nevertheless, because it continues to be desirable to improve the activity of Fischer-Tropsch catalysts, other types of catalyst supports have been investigated.

The use of divinylbenzene cross-linked polystyrene as a support for Fischer-Tropsch catalysts is disclosed in U.S. Pat. No. 4,292,415 and U.S. Pat. No. 4,725,568. Similarly, U.S. Pat. No. 4,230,633 discloses polymer supported metal complexes wherein the ligand is a cycloalkadienyl radical with metals from Group VIII of the Periodic Table. This patent relates to the conversion of carbon monoxide and hydrogen to hydrocarbons in a liquid reaction medium. Nevertheless, despite the research in this field, there is still a desire to identify new, more effective catalysts. In particular, catalysts that provide high $C_{5+}$ and $C_{11+}$ productivities are desired.

SUMMARY OF THE INVENTION

The present invention provides a catalyst system that is effective for producing $C_{5+}$ and $C_{11+}$ hydrocarbons. In accordance with a preferred embodiment, the present catalyst comprises (1) cobalt and at least one other metal selected from the group consisting of silver, iron, zinc and zirconium and (2) a matrix structure comprising a polymer selected from the group consisting of polyacrylates and polymethacrylates. The catalyst so formed is preferably treated with hydrogen at a temperature of at least 400° C. prior to use. Catalyst systems constructed in accordance with the invention compare favorably to previously known catalysts in activity and durability.

The present invention further comprises a process for using the present catalyst system to produce hydrocarbons. The process comprises contacting a feed stream comprising hydrogen and carbon monoxide with the present catalyst system in a reaction zone maintained at conditions that are effective to produce an effluent stream comprising hydrocarbons.

DETAILED DESCRIPTION

The present catalyst system comprises a catalytic composition integrated into a polymeric matrix structure. The catalytic composition preferably comprises at least one Group VIII metal, namely iron, nickel, cobalt, rhenium, ruthenium, chromium, and iridium or mixtures thereof, and at least one other metal selected from the group consisting of silver, iron, zinc and zirconium. Of these, cobalt/silver is most preferred. The catalytic composition may further include one or more promoters selected from the group consisting of alkali and alkaline earth metal in free or combined form, boron, and mixtures thereof.

The polyacrylate and polymethacrylate matrix structures used in the process of this invention can be prepared by the polymerization of metal acrylates and/or metal methacrylates. Several alternative techniques are suitable for achieving the desired polymerization.

Formation of Cobalt acrylate

In one preferred technique, the present catalysts are formed by mixing the desired monomer with a salt of the desired metal catalyst and an initiator in a solvent. Polymerization occurs with mixing, producing a polymerized mass. The metal salt is preferably suspended in water and reacted with the acrylic acid or methacrylic acid at a temperature between about 40 and about 60° C. By way of example only, suitable metal salts include but are not limited to: basic cobalt carbonate, silver carbonate or silver oxide, iron carbonate or iron oxide, zinc carbonate or zinc oxide and zirconium carbonate or zirconium hydroxide. The reactions are carried out for about 5 hours with gradual addition of the acrylic acid or methacrylic and constant stirring. The solid product is extracted with ethanol and the extract is filtered and evaporated to dryness.

Technique I

The present catalysts can be prepared by dissolving a metal acrylate or metal methacrylate, such as cobalt acrylate, cobalt carbonate, or cobalt methacrylate (described above) and at least one other metal acrylate or methacrylate in methanol, ethanol or another suitable alcohol. The alcohol can contain as much as 25 wt % water. The polymerization is preferably carried out at reflux temperature using 2,2'-azobisisobutyronitrile as an initiator. The polymerization reaction mixture is refluxed for at least 3 hours with constant stirring. The reaction product is filtered off, washed several times with ethanol and then dried under vacuum at 40 to 60° C.

Technique II

Alternatively, the present catalysts can be prepared by dissolving polyacrylic acid or polymethacrylic acid in water, followed by addition of the cobalt and at least one metal acrylate or metal methacrylate to the polymer solution under stirring. The solution gels and is evaporated to dryness.

Catalyst

The metal-containing polyacrylate or polymethacrylate catalysts produced by any of the preceding techniques are preferably reduced with hydrogen at a temperature of at least 400° C. before use as a Fischer-Tropsch catalyst. Treatment with hydrogen activates the catalyst. Catalysts produced in this manner do not require supports.

Operation

The present catalysts are preferably used in a Fischer-Tropsch reactor charged with feed gases comprising hydrogen or a hydrogen source and carbon monoxide. H2/CO mixtures suitable as a feedstock for conversion to hydrocarbons according to the process of this invention can be obtained from light hydrocarbons such as methane by means of steam reforming or partial oxidation. The hydrogen is preferably provided by free hydrogen, although some Fischer-Tropsch catalysts have sufficient water gas shift activity to convert some water to hydrogen for use in the Fischer-Tropsch process. It is preferred that the mole ratio of hydrogen to carbon monoxide in the feed be greater than 0.5:1 (e.g., from about 0.67:1 to 2.5:1). The feed gas may also contain carbon dioxide or other compounds that are inert under Fischer-Tropsch reaction conditions, including but not limited to nitrogen, argon, or light hydrocarbons. The feed gas stream should contain a low concentration of compounds or elements which have a deleterious effect on the catalyst. The feed gas may need to be treated to ensure low concentrations of sulfur or nitrogen compounds such as hydrogen sulfide, ammonia and carbonyl sulfides.

The feed gas is contacted with the catalyst in a reaction zone. Mechanical arrangements of conventional design may be employed as the reaction zone. For example, fixed bed, slurry phase, slurry bubble column, fluidized bed, or ebulliating bed reactors. Accordingly, the size of the catalyst particles may vary depending on the reactor in which they are to be used.

The process is typically run in a continuous mode. In this mode, typically, the gas hourly space velocity through the reaction zone may range from about 100 volumes/hour/volume catalyst (v/hr/v) to about 10,000 v/hr/v, preferably from about 300 v/hr/v to about 2,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably, from 80 psig (653 kPa) to about 600 psig (4237 kPa), more preferably, from about 140 psig (1066 kPa) to about 400 psig (2858 kPa).

The reaction products will have a large range of molecular weights. The present catalysts are particularly useful for making hydrocarbons having five or more carbon atoms, especially when the above-referenced space velocity, temperature and pressure ranges are employed.

The wide range of hydrocarbon species produced in the reaction zone will typically result in liquid phase products at the reaction zone operating conditions. Therefore, the effluent stream of the reaction zone will often be a mixed phase stream. The effluent stream of the reaction zone may be cooled to effect the condensation of additional amounts of hydrocarbons and passed into a vapor-liquid separation zone. The vapor phase material may be passed into a second stage of cooling for recovery of additional hydrocarbons. The liquid phase material from the initial vapor-liquid separation zone together with any liquid from a subsequent separation zone may be fed into a fractionation column. Typically, a stripping column is employed first to remove light hydrocarbons such as propane and butane. The remaining hydrocarbons may be passed into a fractionation column wherein they are separated by boiling point range into products such as naphtha, kerosene and fuel oils. Hydrocarbons recovered from the reaction zone and having a boiling point above that of the desired products may be passed into conventional processing equipment such as a hydrocracking zone in order to reduce their molecular weight. The gas phase recovered from the reactor zone effluent stream after hydrocarbon recovery may be partially recycled if it contains a sufficient quantity of hydrogen and/or carbon monoxide.

Without further elaboration, it is believed that one skilled in the art can, using the description herein, utilize the present invention to its fullest extent. The following embodiments are to be construed as illustrative, and not as constraining the remainder of the disclosure in any way whatsoever.

EXAMPLES

Catalyst Reduction

Each of the catalyst samples described below was treated with hydrogen as follows, prior to use in the Fischer-Tropsch reaction. The catalyst sample was placed in a small quartz crucible in a chamber and purged with 0.8 l/min nitrogen at room temperature for 15 minutes. The sample was then heated under 0.7 l/min hydrogen at 1° C./minute to 100° C. and held at 100° C. for one hour. The catalysts were then heated at 1° C./minute to 400° C. and held at 400° C. for four hours under 0.7 l/min hydrogen. The samples were cooled in hydrogen and purged with nitrogen before use.

General Procedure For Batch Tests

For the batch tests, a 2 mL pressure vessel was heated at 225° C. under 1000 psig (6994 kPa) of H2:CO (2:1) and maintained at that temperature and pressure for 1 hour. In a typical run, roughly 50 mg of the hydrogen catalyst and 1 mL of n-octane was added to the vessel. After one hour, the reactor vessel was cooled in ice, vented, and an internal standard of di-n-butylether was added. The reaction product was analyzed on an HP6890 gas chromatograph. Hydrocarbons in the range of C1–C40 were analyzed relative to the internal standard. The lower hydrocarbons were not analyzed since they are masked by the solvent and are also vented as the pressure is reduced.

A C11+ Productivity (g C11+/hour/kg catalyst) was calculated based on the integrated production of the C11–C40 hydrocarbons per kg of catalyst per hour. The logarithm of the weight fraction for each carbon number $\ln(W_n/n)$ was plotted as the ordinate vs. number of carbon atoms in $(W_n/n)$ as the abscissa. The results of runs over a variety of catalysts at 225° C. are set out below in Table 1.

Catalyst Preparation

Basic cobalt carbonate [CoCO3[Co(OH)2]n·2H2O] (40 g) was suspended in water (400 mL). Acrylic acid (25 mL) was added dropwise with stirring to the cobalt carbonate suspension and heated to 50–60° C. in a waterbath. The black mass produced was extracted with ethanol, filtered, and evaporated to dryness yielding a purple solid, which was Co-acrylate.

EXAMPLE 1

A sample of the Co-acrylate (15.8 g) and Ag-acrylate (commercially available, 1 g) were dissolved in ethanol along with 2,2'-azobisisobutyronitrile (AIBN, 0.2 g) initiator. The mixture was refluxed for 3.5 hours. The brownish precipitate was filtered, washed with warm ethanol and dried in a rotary evaporator at 55° C. This material was reduced in hydrogen at 400° C. before use.

EXAMPLE 2

Co-acrylate was dissolved in ethanol to prepare 25 mL of a solution containing 20 weight percent Co-acrylate, and placed in a 3-necked flask. Fe-acrylate (commercially available, 1 g) was dissolved in aqueous ethanol with stirring and heating and added to the flask. AIBN initiator (0.2 g) was added and the mixture was refluxed for 4 hours. The brown precipitate was filtered, washed with warm ethanol and dried in a rotary evaporator at 55° C. This material was reduced in hydrogen at 400° C. before use.

EXAMPLE 3

Co-acrylate (6 g) was dissolved in ethanol and was placed in 3-necked flask. Zn-acrylate (commercially available, 1 g) was dissolved in aqueous ethanol with stirring and heating and added to the flask. AIBN initiator (0.2 g) was added and the mixture was refluxed for 4 hours. The pink-purple precipitate was filtered, washed with warm ethanol and dried in a rotary evaporator at 55° C. This material was reduced in hydrogen at 400° C. before use.

EXAMPLE 4

Co-acrylate was dissolved in ethanol to prepare 25 mL of a solution containing 20 weight percent Co-acrylate, and placed in a 3-necked flask. Zr-acrylate (commercially available, 1 g) was dissolved in aqueous ethanol with stirring and heating and added to the flask. AIBN initiator (0.2 g) was added and the mixture was refluxed for 4 hours. The purple precipitate was filtered, washed with warm ethanol and dried in a rotary evaporator at 55° C. This material was reduced in hydrogen at 400° C. before use.

EXAMPLE 5

Co-acrylate (5 g) was dissolved in ethanol to prepare 20 weight % Co acrylate solution and placed in a three-necked flask. Cr-acrylate (commercially available, 1 g) was dissolved in 75% aqueous ethanol with stirring and heating and added to the flask. AIBN initiator (0.2 g) dissolved in ethanol was added, and the mixture was refluxed for 4 hours. The gray-blue precipitate was filtered, washed with warm ethanol and dried in a rotary evaporator at 55° C. This material was reduced in hydrogen at 400° C. before use.

EXAMPLE 6

Co-acrylate (5 g) was dissolved in ethanol to prepare 20 weight % Co acrylate solution and placed in a three-necked flask. Cr-methacrylate (commercially available, 1 g) and Ag-methacrylate (commercially available, 1 g) were dissolved in 75% aqueous ethanol with stirring and heating and added to the flask. AIBN initiator (0.2 g) dissolved in ethanol was added, and the mixture was refluxed for 4 hours. The brown precipitate was filtered, washed with warm ethanol and dried in a rotary evaporator at 55° C. This material was reduced in hydrogen at 400° C. before use.

EXAMPLE 7

Polyacrylic acid (commercially available, M.W. 250,000, 2.5 g) was dissolved in H2O (60 mL). Ag-acrylate (0.1 g) was dissolved in aqueous ethanol (40 mL, 25% H2O) and added to the polyacrylic acid solution. A Co-acrylate solution in ethanol (10 mL, 0.25 g/mL) was added with stirring. The solution gelled and was evaporated to dryness. This material was reduced in hydrogen at 400° C. before use.

TABLE 1

| Ex. | Catalyst | $C_{11+}$ Productivity |
|---|---|---|
| 1 | Poly(Co, Ag acrylate) | 241 |
| 2 | Poly(Co—Fe acrylate) | 33.5 |
| 3 | Poly(Co—Zn acrylate) | 210 |
| 4 | Poly(Co—Zr acrylate) | 23.1 |
| 5 | Poly(Co—Cr acrylate) | 33.8 |
| 6 | Poly(Co—acrylate/Cr—ethacrylate/ Ag—methacrylate) | 67.5 |
| 7 | Polyacrylic acid/Co, Ag—acrylate | 142 |

Comparative Example A

A sample of the Co-acrylate (3.1 g) was dissolved in ethanol (30 mL) along with 2,2'-azobisisobutyronitrile (AIBN, 0.06 g) initiator. The mixture was refluxed for 3.5 hours. The precipitate was filtered, washed with warm ethanol and dried in a rotary evaporator at 50° C. The sample was reduced in hydrogen before use.

Comparative Example B

A sample of the Co-acrylate (15.8 g) and Ag-acrylate (commercially available, 1 g) were dissolved in ethanol along with 2,2'-azobisisobutyronitrile (AIBN, 0.2 g) initiator. The mixture was refluxed for 3.5 hours. The brownish precipitate was filtered, washed with warm ethanol and dried in a rotary evaporator at 55° C. This material was reduced in hydrogen at 200° C. before use.

Comparative Example C

A sample of the Co-acrylate (15.8 g) and Ag-acrylate (commercially available, 1 g) were dissolved in ethanol along with 2,2'-azobisisobutyronitrile (AIBN, 0.2 g) initiator. The mixture was refluxed for 3.5 hours. The brownish precipitate was filtered, washed with warm ethanol and dried in a rotary evaporator at 55° C. This material was reduced in hydrogen at 300° C. before use.

Comparative Example D

Polyacrylic acid (commercially available, M.W. 250,000, 2.0 g) was dissolved in H2O (60 mL). The solution was evaporated to dryness. This material was reduced in hydrogen at 400° C. before use.

Comparative Example E

Ethanolic Co-acrylate solution (20 wt % Co-acrylate in ethanol, 25 mL) was placed in a 3-necked flask. Cu-acrylate (commercially available, 1 g) was dissolved in aqueous ethanol with stirring and heating and added to the flask. AIBN initiator (0.1 g) was added and the mixture was refluxed for 4 hours. The gray precipitate was filtered, washed with warm ethanol and dried in a rotary evaporator at 55° C. before use.

None of the materials prepared in Comparative Example A to E were catalytically active.

What is claimed is:

1. A process for producing hydrocarbons, comprising contacting a feed stream comprising hydrogen and carbon monoxide with a catalyst in a reaction zone maintained at conversion-promoting conditions effective to produce an effluent stream comprising hydrocarbons, wherein the catalyst comprises:
    a catalytically active first metal selected from the group consisting of at least one metal selected from the group consisting of iron, nickel, cobalt, chromium, and mixtures thereof;
    at least one second metal selected from the group consisting of silver, iron, zinc and zirconium and combinations thereof; and
    a matrix structure comprising a polymer selected from the group consisting of polyacrylates and polymethacrylates;
    wherein the first and second metals are incorporated into the polymer.

2. The process of claim 1 wherein the first metal is cobalt.

3. The process of claim 2 wherein the second metal is silver.

4. The process of claim 1 wherein the first metal comprises from about 0.1 to 50 mole percent of the matrix metal and catalyst metal combined.

5. The process of claim 4 wherein the first metal comprises from about 10 to 50 mole percent of the matrix metal and catalyst metal combined.

6. The process of claim 1 wherein the catalyst comprises a polymer selected from the group consisting of poly(Co, Ag-acrylate), poly(Co—Fe acrylate), poly(Co—Zn acrylate), poly(Co—Zr acrylate), poly(Co—Cr acrylate), poly(Co—acrylate/Cr-ethacrylate/Ag-methacrylate) and polyacrylic acid/ Co,Ag-acrylate.

7. The process of claim 6 wherein the polymer is pretreated in hydrogen.

8. The process of claim 6 wherein the polymer is pretreated in hydrogen at a temperature above 300° C. for at least 0.5 hours.

9. A process for producing hydrocarbons by contacting a feed stream comprising hydrogen and carbon monoxide with a catalyst in a reaction zone maintained at conversion-promoting conditions effective to produce an effluent stream comprising said hydrocarbons, wherein the catalyst is prepared by:
    (a) providing a catalytically active first metal selected from the group consisting of at least one metal selected from the group consisting of iron, nickel, cobalt, chromium, and mixtures thereof;
    (b) providing at least one second metal selected from the group consisting of silver, iron, zinc and zirconium and combinations thereof; and
    (c) providing a polymer precursor; and
    (d) polymerizing the polymer precursor in the presence of said first and second metals to form a polymer selected from the group consisting of polyacrylates and polymethacrylates, such that the first and second metals are incorporated into the polymer.

10. The process of claim 9 wherein the first metal is cobalt.

11. The process of claim 10 wherein the second metal is silver.

12. The process of claim 9 further including treating the polymer in hydrogen.

13. The process of claim 9 further including treating the polymer in hydrogen at a temperature above 300° C. for at least 0.5 hours.

14. The method of claim 9 wherein the polymer is selected from the group consisting of poly(Co,Ag-acrylate), poly(Co—Fe acrylate), poly(Co—Zn acrylate), and poly(Co—Zr acrylate), poly(Co—acrylate/Cr-ethacrylate/Ag-methacrylate) and polyacrylic acid/ Co,Ag-acrylate.

* * * * *